(12) United States Patent
Jeon

(10) Patent No.: US 10,302,423 B2
(45) Date of Patent: May 28, 2019

(54) THREE-DIMENSIONAL SHAPE MEASUREMENT APPARATUS

(71) Applicant: KOH YOUNG TECHNOLOGY INC., Seoul (KR)

(72) Inventor: Moon Young Jeon, Seongnam-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 0 days.

(21) Appl. No.: 15/735,021

(22) PCT Filed: Jun. 3, 2016

(86) PCT No.: PCT/KR2016/005891
§ 371 (c)(1),
(2) Date: Dec. 8, 2017

(87) PCT Pub. No.: WO2016/200096
PCT Pub. Date: Dec. 15, 2016

(65) Prior Publication Data
US 2018/0156606 A1    Jun. 7, 2018

(30) Foreign Application Priority Data

Jun. 8, 2015 (KR) ........................ 10-2015-0080284

(51) Int. Cl.
| | | |
|---|---|---|
| *G01B 11/25* | (2006.01) | |
| *G01B 11/02* | (2006.01) | |
| *G01B 11/245* | (2006.01) | |
| *G01N 21/956* | (2006.01) | |
| *G06T 7/521* | (2017.01) | |

(Continued)

(52) U.S. Cl.
CPC .......... *G01B 11/2513* (2013.01); *G01B 11/02* (2013.01); *G01B 11/245* (2013.01);
(Continued)

(58) Field of Classification Search
None
See application file for complete search history.

(56) References Cited

U.S. PATENT DOCUMENTS

| | | |
|---|---|---|
| 2003/0042401 A1 | 3/2003 | Gartner et al. |
| 2007/0177159 A1* | 8/2007 | Kim .................. G01B 11/2531 356/601 |

(Continued)

FOREIGN PATENT DOCUMENTS

| | | |
|---|---|---|
| EP | 2 175 233 | 4/2010 |
| KR | 10-2005-0031328 | 4/2005 |

(Continued)

OTHER PUBLICATIONS

International Search Report for International Application No. PCT/KR2016/005891, dated Sep. 8, 2016.

(Continued)

*Primary Examiner* — Frederick D Bailey
(74) *Attorney, Agent, or Firm* — Kile Park Reed & Houtteman PLLC

(57) ABSTRACT

A three-dimensional shape measurement apparatus includes main pattern illumination parts, main image-capturing parts and a control part. The main pattern illumination parts obliquely illuminate grating pattern light in different directions toward a measurement target. The main image-capturing parts obtain a grating pattern image of the measurement target by receiving reflection light of the grating pattern light illuminated from the main pattern illumination parts and obliquely reflected by the measurement target. The control part produces height data of the measurement target using grating pattern images of the measurement target, or produces height data of the measurement target using image positions of plane images for the measurement target and texture information of the measurement target. The control part employs a grating pattern illuminated on the measurement target as the texture information to produce height data of the measurement target. Thus, a three-dimensional shape may be measured more easily and accurately.

11 Claims, 7 Drawing Sheets

(51) Int. Cl.
  *G06T 7/593* (2017.01)
  *H04N 13/254* (2018.01)
  *H04N 13/243* (2018.01)
  *H04N 13/239* (2018.01)

(52) U.S. Cl.
  CPC ........ *G01B 11/254* (2013.01); *G01B 11/2545* (2013.01); *G01N 21/95684* (2013.01); *G06T 7/521* (2017.01); *G06T 7/593* (2017.01); *H04N 13/239* (2018.05); *H04N 13/243* (2018.05); *H04N 13/254* (2018.05); *G01N 2021/95638* (2013.01)

(56) References Cited

U.S. PATENT DOCUMENTS

| | | | |
|---|---|---|---|
| 2010/0091301 A1 | 4/2010 | Masuda | |
| 2010/0277571 A1* | 11/2010 | Xu | ............................ G06T 17/00 348/47 |
| 2012/0056982 A1 | 3/2012 | Katz et al. | |
| 2014/0198185 A1 | 7/2014 | Haugen et al. | |

FOREIGN PATENT DOCUMENTS

| | | | |
|---|---|---|---|
| KR | 10-2007-0122014 | 12/2007 | |
| KR | 10-2013-0130565 | 12/2013 | |
| KR | 10-2013-0130656 | 12/2013 | |
| WO | 2012/134146 | 10/2012 | |
| WO | WO-2013036076 A2 * | 3/2013 | ............. G01B 11/25 |

OTHER PUBLICATIONS

Daniel Scharstein et al.; "High-Accuracy Stereo Depth Maps Using Structured Light"; Proceedings of the 2003 IEEE Computer Society Conference on Computer Vision and Pattern Recognition; (CVPR '03).

Supplementary European Search Report for European Application No. EP 16 80 7737, dated Mar. 26, 2018.

* cited by examiner

THREE-DIMENSIONAL SHAPE MEASUREMENT APPARATUS

TECHNICAL FIELD

The present invention relates to a three-dimensional shape measurement apparatus. More particularly, the present invention relates to a three-dimensional shape measurement apparatus measuring a three-dimensional shape based on height.

BACKGROUND ART

Generally, at least one printed circuit board (PCB) is employed in an electronic device, and various shaped elements are mounted on the PCB. In order to inspect defects of these elements, a three-dimensional shape measurement apparatus is typically used.

A conventional three-dimensional shape measurement apparatus illuminates light to a measurement target such as a PCB by using an imaging optical system, and image-captures a reflection image thereof using a camera. Then, a three-dimensional shape based on the height of the measurement target is measured using the captured reflection image.

Conventional imaging optical systems may be configured in various configurations. An optical triangulation method, a stereo method, etc. among the various configurations may be employed in the imaging optical system.

The optical triangulation method is a method using such as a bucket algorithm after acquiring a grating pattern, and widely used at present. However, this method has a problem that the height that is measurable is restricted by a pitch of a grating generating the pattern image.

The stereo method uses a stereo camera. Just as a person's perspective to an object can be perceived by synthesizing information input through two eyes into distance information, a stereo camera may also calculate three-dimensional distance information by capturing images from two cameras.

That is, a three-dimensional shape may be measured by using two or more images obtained by photographing at different positions. Particularly, in the two images including texture of a measurement target on a real space, position information of the measurement target in the real space of the measurement target is obtained by using a geometric structure based on the texture, to thereby measure the three-dimensional shape of the measurement target.

Thus, in case that the measurement target has texture, the three-dimensional shape of the measurement target may be measured based on the texture, but in case that the surface of the measurement target is smooth, since it is impossible to use a geometric structure based on the texture of the measurement target, the stereo method may be unavailable.

DISCLOSURE

Technical Problem

Accordingly, the present invention provides a three-dimensional shape measurement apparatus capable of measuring a three-dimensional shape of a measurement target by using a stereo method even though there is no texture or unclear texture.

Technical Solution

According to an exemplary embodiment of the present invention, a three-dimensional shape measurement apparatus includes a plurality of main pattern illumination parts, a plurality of main image-capturing parts and a control part. The main pattern illumination parts obliquely illuminate grating pattern light in different directions toward a measurement target. The main image-capturing parts obtain a grating pattern image of the measurement target by receiving reflection light of the grating pattern light that is illuminated from the main pattern illumination parts to the measurement target and obliquely reflected by the measurement target. The control part produces height data of the measurement target by using grating pattern images of the measurement target, or produces height data of the measurement target by using image positions of plane images for the measurement target and texture information of the measurement target. The control part employs a grating pattern illuminated on the measurement target as the texture information to produce height data of the measurement target.

In an exemplary embodiment, the three-dimensional shape measurement apparatus may further include an illumination part illuminating light toward the measurement target. The plurality of main image-capturing parts obtain a plane image of the measurement target by receiving reflection light of the light that is illuminated from the illumination part to the measurement target and reflected by the measurement target.

In an exemplary embodiment, the plane images of the measurement target may be image-captured without the grating pattern light or obtained by averaging the grating pattern images.

In an exemplary embodiment, the grating pattern may be employed as the texture information to produce the height data of the measurement target in case that there is no texture information of the measurement target.

In an exemplary embodiment, the control part may produce the height data of the measurement target by using the grating pattern images of the measurement target with respect to less than a reference height, and produce the height data of the measurement target by using the image positions of the plane images for the measurement target and the texture information of the measurement target with respect to the reference height or higher. For example, the reference height may be less than or equal to a measurable height according to the grating pattern light of the main pattern illumination parts. Meanwhile, at least two of the main pattern illumination parts may include gratings having different grating pitches to generate grating pattern lights having different equivalent wavelengths, and the reference height may be less than or equal to an integrated measurable height according to the different equivalent wavelengths.

In an exemplary embodiment, the three-dimensional shape measurement apparatus may further include a top pattern illumination part disposed over the measurement target to perpendicularly illuminate grating pattern light toward the measurement target.

In an exemplary embodiment, the three-dimensional shape measurement apparatus may further include a top image-capturing part disposed over the measurement target to obtain the grating pattern image of the measurement target by receiving reflection light of the grating pattern light that is perpendicularly reflected by the measurement target. The control part may produce the height data of the measurement target by using the grating pattern image obtained between the top image-capturing part and each main image-capturing part.

In an exemplary embodiment, the main pattern illumination parts may be spaced apart from each other along circumferential direction around the measurement target, and the main image-capturing parts may be spaced apart from each other along circumferential direction about the measurement target. Herein, the main pattern illumination parts and the main image-capturing parts may form one set and may be arranged in correspondence with each other.

According to another exemplary embodiment of the present invention, a three-dimensional shape measurement apparatus includes a plurality of main pattern illumination parts, a plurality of main image-capturing parts and a control part. The main pattern illumination parts obliquely illuminates grating pattern light in different directions toward a measurement target. The main image-capturing parts obtain a grating pattern image of the measurement target by receiving reflection light of the grating pattern light that is illuminated from the main pattern illumination parts to the measurement target and obliquely reflected by the measurement target. The control part produces height data of the measurement target by selectively applying a first method of producing the height data of the measurement target by using the grating pattern image of the measurement target, a second method of producing the height data of the measurement target by using image positions of plane images for the measurement target and texture information of the measurement target, and a third method of producing the height data of the measurement target by utilizing the grating pattern illuminated on the measurement target as the texture information of the measurement target.

For example, the control part may determine which of the first, second, and third methods to apply.

Advantageous Effects

According to the present invention, in measuring a three-dimensional shape of a measurement target, an optical triangulation method and a stereo measurement method are both or selectively used, in which grating pattern illuminated on the measurement target may be used as texture information of the measurement target in case that it is difficult to utilize the texture information, to thereby measure the three-dimensional shape more easily and accurately.

In addition, in duality based on a predetermined reference height, the optical triangulation method may be used for less than the reference height to produce height data, and the stereo measurement method may be used for greater than or equal to the reference height to produce height data, to thereby maintain measurement accuracy at low height while extending a range of measurable heights.

In addition, by generating grating pattern light from multiple pattern illumination parts and capturing grating pattern images in multiple image-capturing parts, more accurate and precise three-dimensional shape measurement may be available at various directions and angles according to an optical triangulation method and a stereo measurement method.

MODE FOR INVENTION

Figure 1:
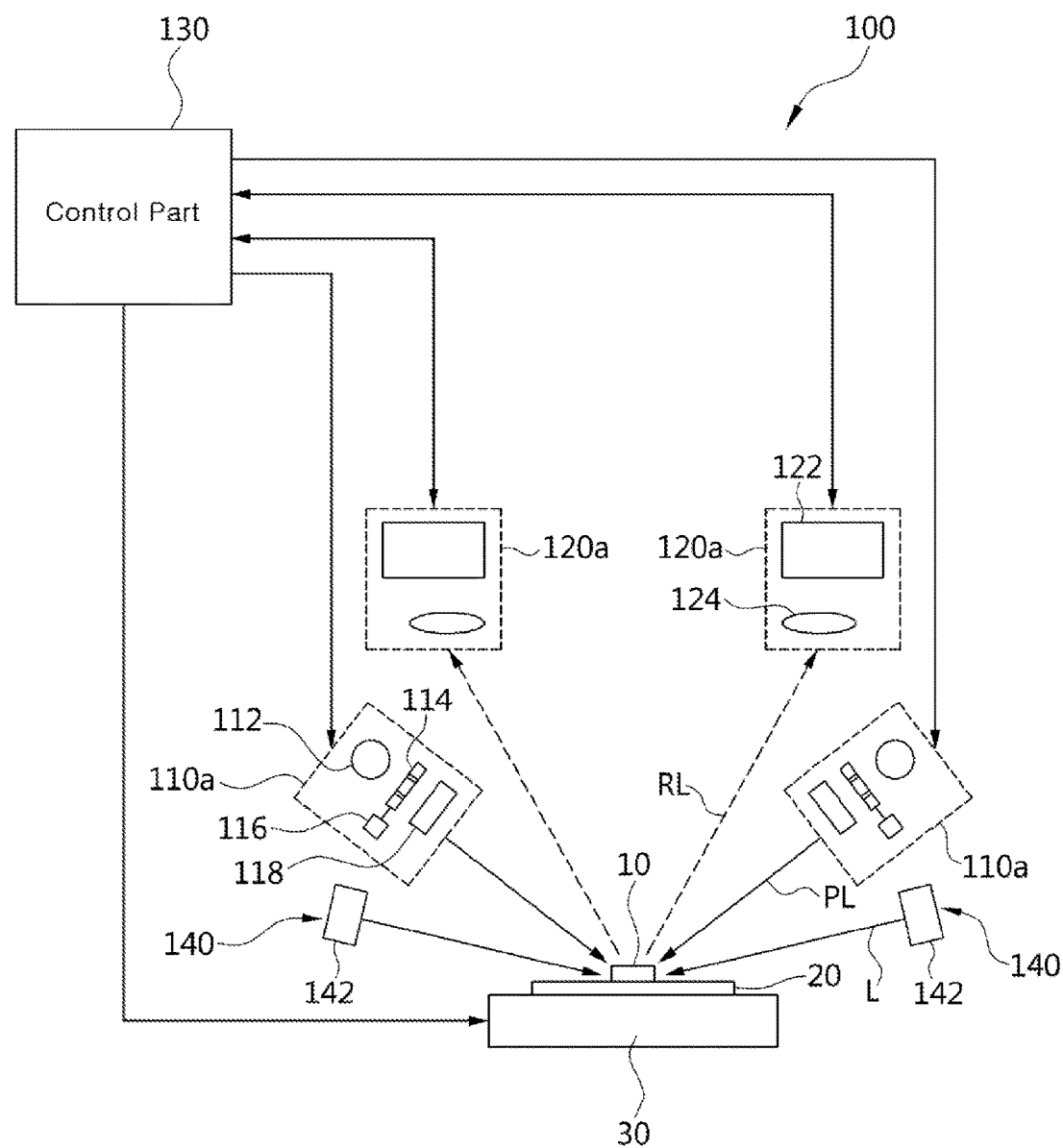
FIG. 1 is a front view schematically showing a three-dimensional shape measurement apparatus according to an exemplary embodiment of the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that, although the terms first, second, third etc. may be used herein to describe various elements, components, regions, layers and/or sections, these elements, components, and/or sections should not be limited by these terms. These terms are only used to distinguish one element, component, region, layer or section from another region, layer or section. Thus, a first element, component, or section discussed below could be termed a second element, component, or section without departing from the teachings of the present invention.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, with reference to the drawings, preferred embodiments of the present invention will be described in detail.

Figure 2:
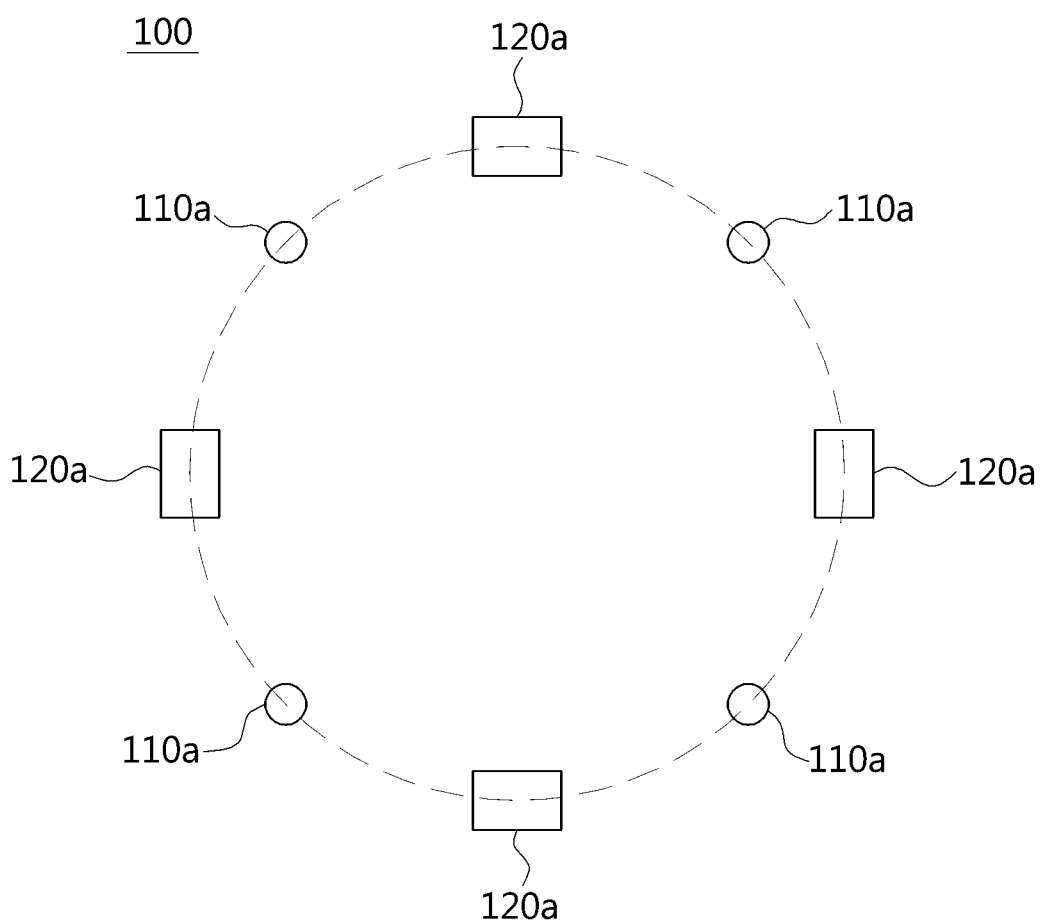
FIG. 2 is a plan view of the three-dimensional shape measurement apparatus shown in FIG. 1.

FIG. 1 is a front view schematically showing a three-dimensional shape measurement apparatus according to an exemplary embodiment of the present invention. FIG. 2 is a plan view of the three-dimensional shape measurement apparatus shown in FIG. 1.

Referring to FIGS. 1 and 2, a three-dimensional shape measurement apparatus 100 according to an exemplary embodiment of the present invention may include a plurality of main pattern illumination parts 110a, a plurality of main image-capturing parts 120a, and a control part 130, etc.

The main pattern illumination parts 110a obliquely illuminate grating pattern light PL in different directions towards the measurement target 10. In other words, the main pattern illumination parts 110a may illuminate the grating pattern light PL for obtaining three-dimensional shape information of the measurement target 10 with the grating pattern light PL being inclined with respect to a normal perpendicular to the plane of the measurement target.

The measurement target 10 may include solder or components formed on a board 20 such as a printed circuit board (PCB). The board 20 may be disposed and supported on a stage 30. The stage 30 may transfer the measurement target 10 to a measurement position by a transfer device (not shown).

In one embodiment, the main pattern illumination parts 110a may illuminate the grating pattern light PL toward the measurement target 10 by N times, and a grating pattern may be transferred N times by using a grating transfer instrument or by using a pattern image of a liquid crystal display (LCD) device to illuminate a phase-shifted grating pattern light. In the main image-capturing part 120a described later, grating pattern images according to illuminated grating pattern lights PL may be obtained.

In one embodiment, each of the main pattern illumination parts 110a may include a light source 112, a grating 114, a grating transfer instrument 116, and a projection lens portion 118.

The light source 112 illuminates light towards the measurement target 10. The grating 114 converts the light emitted from the light source 112 into the grating pattern light PL. The grating 114 is moved N times by $2\pi/N$ through the grating transfer instrument 116, for example, such as a piezo actuator (PZT), so as to generate a phase-shifted grating pattern light PL (N is a natural number not less than 2). The projection lens portion 118 projects the grating pattern light PL generated by the grating 114 onto the measurement target 10. The projection lens portion 118 may include, for example, a plurality of lens combinations, and focuses the grating pattern light PL formed through the grating 114 onto the measurement target 10. Thus, each main pattern illumination part 110 provides the grating pattern light PL to the measurement target 10 at each transfer, while transferring the grating 114 N times.

In one embodiment, the three-dimensional shape measurement apparatus 100 may include four main pattern illumination parts 110a, as shown in FIG. 2. The four main pattern illumination parts 110a may be spaced apart from each other around the measurement target 10 in the circumferential direction or arranged at respective vertexes of a polygon around the measurement target 10, when the measurement target 10 is viewed in a plan view. Thus, the main pattern illumination parts 110a may be provided in various numbers, for example, such as two, four, eight, etc.

The main image-capturing parts 120a capture a grating pattern image of the measurement target 10 by receiving reflection light RL of grating pattern light, which is illuminated from the main pattern illumination parts 110a and obliquely reflected by the measurement target 10.

In one embodiment, each of the main image-capturing parts 120a may include a camera 122 and an imaging lens 124. For example, the camera 122 may employ a CCD or a CMOS camera. The reflection light RL of the grating pattern light, which is reflected from the measurement target 10 may be imaged by the imaging lens 124 and captured by the camera 122.

In one embodiment, the three-dimensional shape measurement apparatus 100 may include four main image-capturing parts 120a, as shown in FIG. 2. The four main image-capturing parts 120a may be spaced apart from each other around the measurement target 10 in the circumferential direction or arranged at respective vertexes of a polygon around the measurement target 10, when the measurement target 10 is viewed in a plan view. Thus, the main image-capturing parts 120a may be provided in various numbers, for example, such as two, four, eight, etc.

The main pattern illumination parts 110a and the main image-capturing parts 120a may be disposed alternately with each other, as shown in FIG. 2. In one embodiment, the four main pattern illumination parts 110a and the four main image-capturing parts 120a may be alternately and equally spaced apart from each other at eight positions around the circumference, when the measurement target 10 is viewed in a plan view. In FIG. 2, the main pattern illumination parts 110a and the main image-capturing parts 120a are arranged along the circumference of the same circle when viewed in a plan view, but alternatively it is obvious that the main image-capturing parts 120a and the main image capturing parts 120a may be disposed along the circumference of the circles of respectively different radii.

When the main pattern illumination parts 110a and the main image-capturing parts 120a are alternately disposed as described above, the grating pattern images that are formed by the grating pattern lights PL generated from the main pattern illumination parts 110a may be sequentially or simultaneously captured by all of the main image-capturing parts 120a.

Meanwhile, the main pattern illumination parts 110a and the main image-capturing parts 120a may optionally employ optical path changing elements such as a mirror, so that substantial placement positions may be configured as the above, even though actual placement positions are somewhat different from the above.

The control part 130 produces height data of the measurement target 10.

Particularly, the control part 130 may produce the height data of the measurement target 10 by using the grating pattern images of the measurement target 10 captured in the main image-capturing parts 120a. That is, the control part 130 may produce the height data of the measurement target 10 by using an optical triangulation method. For example, the control part 130 may apply the well-known bucket algorithm to the grating pattern images captured in the main image-capturing parts 120a, to obtain the height data of the measurement target 10.

Also, the control part 130 may produce the height data of the measurement target 10 by using the image position of the plane images of the measurement target 10 and texture information of the measurement target 10. That is, the control part 130 may produce the height data of the measurement target 10 by using a stereo method.

Figure 3:
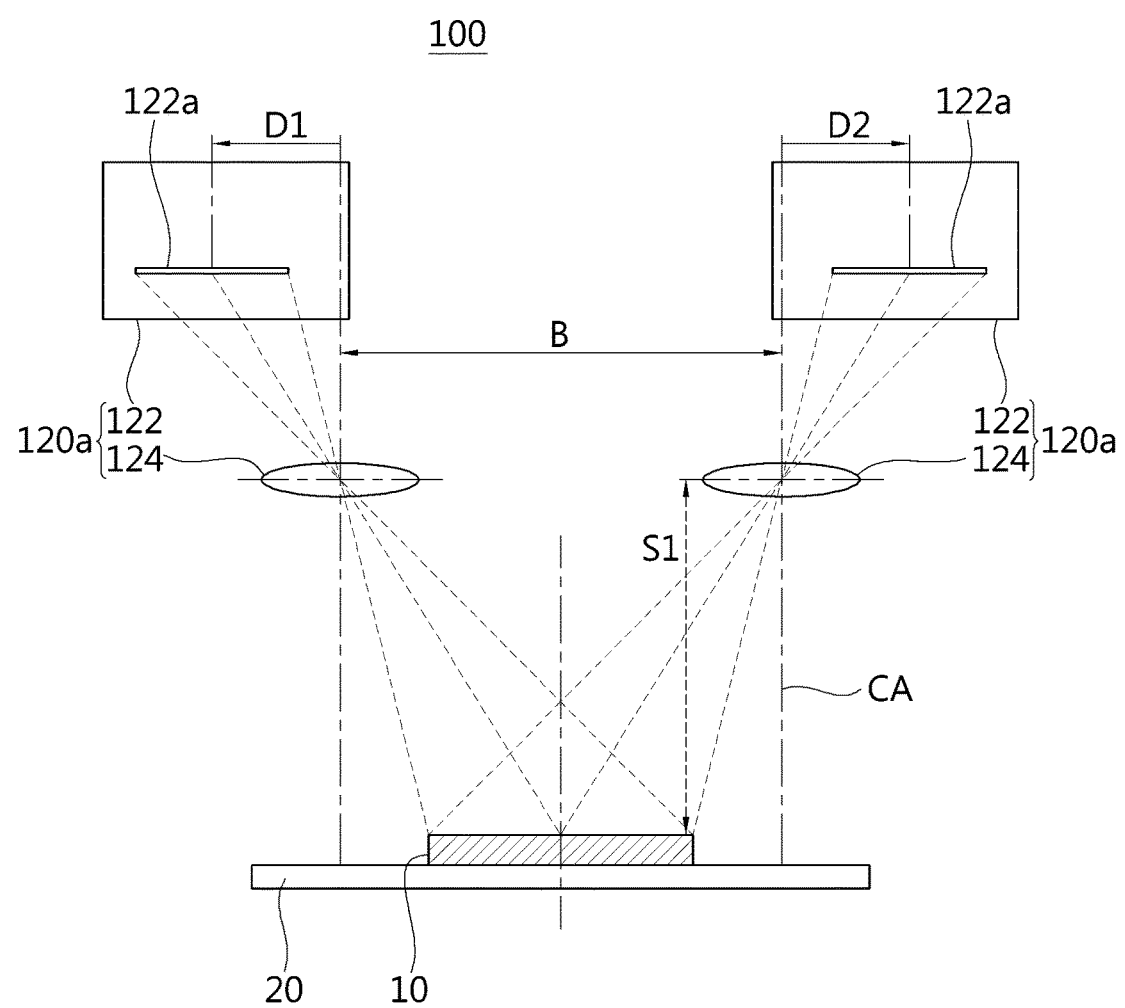
FIG. 3 is a conceptual view for explaining a process of measuring the three-dimensional shape by using a stereo method in the control part of the three-dimensional shape measurement apparatus in FIG. 1.

FIG. 3 is a conceptual view for explaining a process of measuring the three-dimensional shape by using a stereo method in the control part of the three-dimensional shape measurement apparatus in FIG. 1.

Referring to FIG. 3, the measurement target 10 applies a triangular technique to the image position of the measurement target 10 based on an image obtained from at least two image-capturing parts 120a, to thereby obtain the height data of the measurement target 20.

As shown in FIG. 3, the imaging lenses 124 are disposed at a predetermined distance B, and distances D1 and D2 imaged on the image-capturing elements 122a of the cameras 122 are measured based on the center axis CA of the imaging lenses 124. Meanwhile, when the focal length of the imaging lens 124 is 'f', a relationship between the distances and the focal length satisfies Equation 1.

$$S1=fB/|D1-D2| \quad \text{[Equation 1]}$$

Therefore, since a distance S1 from the imaging lens 124 to the measurement target 10 may be known, the height data of the measurement target 10 may be obtained.

Based on the same principle, the control part 130 may obtain the height data of the measurement target 10 from the plane images of the measurement target 10 by using a stereo method.

Herein, at least two plane images captured at different positions, such as the above, may use the texture information of the measurement target 10 to find a matching point indicating the same point in an actual space.

Herein, the grating pattern illuminated on the measurement target (10) may be used as the texture information. For example, when the surface of the measurement target (10) is smooth, the texture information may not be obtained, and thus in case that the texture information may not be obtained, the grating pattern illuminated on the measurement target 10 may be utilized.

Accordingly, in case that there is texture information in the measurement target 10, the texture information may be applied to a stereo method to obtain the height data of the measurement target 10, and in case that there is no texture information in the measurement target 10, the grating pattern illuminated on the measurement target may be employed as the texture information, which is applied to a stereo method, to thereby obtain the height data of the measurement target 10. Of course, even though there is texture information in the measurement target 10, the grating pattern illuminated on the measurement target 10 may be used as the texture information. In addition, since the plane image of the measurement target 10 may be obtained in units of a field of view of the main image-capturing part 120a, only a part of the field of view of the measurement target 10 has no texture information, the grating pattern illuminated on the measurement target 10 may be used as the texture information for the corresponding field of view.

The three-dimensional shape measurement apparatus 100 may further include an illumination part 140 for acquiring a two-dimensional plane image of the measurement target 10. The illumination part 140 is disposed over the board 20 to illuminate light L toward the measurement target 10. For example, the illumination part 140 may include a plurality of illumination units 142 arranged in a circle with respect to a central axis passing through the center of the measurement target 10 when viewed in a plan view. For example, the illumination part 140 may illuminate a plurality of different color lights at different inclination angles, each of which may have LED light continuously arranged to have a ring shape, thereby generating monochromatic illumination.

The main image-capturing parts 120a obtain a plane image of the measurement target 10 by receiving reflection light RL of the light, which is illuminated from the illumination part 140 and reflected by the measurement target 10. The control part 130 may obtain the height data of the measurement target 10 by using the stereo method from the plane images of the measurement target 10 obtained as described above.

Alternatively, the plane images of the measurement target 10 may be obtained by averaging the grating pattern images. Particularly, N grating pattern images may be acquired by grating pattern light PL generated in any one of the main pattern illumination parts 110a, and brightness values of the N grating pattern images are summed and divided by N for each pixel, to thereby obtain a plane image of the measurement target 10 having an average value of brightness values per pixel.

The control part 130 may produce the height data of the measurement target 10 by using the grating pattern images of the measurement target 10 captured in the main image capturing parts 120a, and in this case, since the reflection lights RL of the grating pattern lights PL generated in the 'm' main pattern illumination parts 110a are captured in the 'n' main image-capturing parts 120a, the height data of the measurement target 10 may be produced as m×n. In addition, the control part 130 may produce the height data of the measurement target 10 by using the image position of the plane images of the measurement target 10 and the texture information of the measurement target 10, and in this case, since a stereo method may be applied by using the plane images obtained from the two image-capturing parts 120a of the 'n' main image-capturing parts 120a, the height data of the measurement target 10 may be produced as n(n−1)/2.

As described above, the height data of the measurement target 10 may be obtained in plurality for any one point, so that the plurality of height data may be selectively used or processed to obtain final height data. Also, the control part 130 may produce the height data by selectively applying a first method of producing the height data of the measurement target 10 by using the grating pattern images of the measurement target 10, a second method of producing the height data of the measurement target 10 by using the image position of the plane images of the measurement target 10 and the texture information of the measurement target 10, and a third method of producing the height data of the measurement target 10 by utilizing the grating pattern illuminated on the measurement target 10 as the texture information of the measurement target 10. Herein, the control part 130 may determine which of the first, second, and third methods to apply, and may determine to apply two or more of the methods.

That is, three-dimensional shapes using the methods may be matched with respect to one measurement target, and a more precise three-dimensional shape measurement may be available.

For example, the control part 130 may select images or image pixels with high reliability among the grating pattern images captured by the main image-capturing parts 120a, and combine the selected images or image pixels, to obtain the height data of the measurement target 10.

The reliability may include at least one of brightness, visibility, signal-to-noise ratio (SNR), the measurement range (λ) corresponding to each grating pitch of the grating pattern lights PL, and relative position information between each main image-capturing part 120a and each main pattern illumination part 110a.

Depending on the location of the measurement target 10 in the captured grating pattern image, a shadow region and a saturation region may occur. These shadow region and saturation region are regions having low reliability, and may be excluded when the height data of the measurement target 10 is acquired. For example, the shadow region may be defined as an area in which average brightness is less than a reference brightness value and visibility or SNR is less than a reference value, and the saturation region may be defined as an area in which average brightness is greater than a reference brightness value and visibility or SNR is less than a reference value. The remaining regions except the shadow region and the saturation region may be defined as a non-saturation region, and the non-saturation region may be included in obtaining the height data of the measurement target 10 as a region having high reliability.

In addition, the shadow region and the saturation region may be generated differently depending on the relative positions between the main image-capturing part 120a and the main pattern illumination part 110a. For example, two main pattern illumination parts 110a adjacent to one main image-capturing part 120a and two main pattern illumination parts 110a not adjacent to the one main image-capturing part 120a form different shadow regions and saturation regions. Therefore, the reliability may be set by the relative position information between each main image-capturing part 120a and each main pattern illumination part 110a.

In addition, since the grating pitch of the main pattern illumination parts 110a may determine a measurement range, that is, a measurable height, the reliability of the height data may vary depending on the height of the measurement target 10. Therefore, the reliability may be set based on the grating pitch and the height information of the measurement target 10.

Meanwhile, the control part 130 may set a reference height and produce the height data in duality based on the reference height. Particularly, the control part 130 may produce the height data of the measurement target 10 by using the grating pattern images of the measurement target 10 for less than the reference height, and may produce the height data of the measurement target 10 by using the image position of the plane images of the measurement target 10 and the texture information of the measurement target 10 for greater than the reference height.

Herein, the reference height may be less than or equal to the measurable height according to the grating pattern light PL of the main pattern illumination parts 110a. The measurable height according to the grating pattern light PL means a height, measurement of which is possible, defined by the grating pitch that produces the grating pattern light, as described above.

When the main pattern illumination parts 110a employ multiple wavelengths, at least one of the main pattern illumination parts 110a may have a different grating pitch, or one main pattern illumination part 110a may have two or more different grating pitches. For example, at least two of the main pattern illumination parts 110a may include gratings 114 having different grating pitches, to respectively generate grating pattern light PL having an equivalent wavelength different from each other. In this case, the reference height may be set to less than or equal to an integrated measurable height according to the different equivalent wavelengths.

In this way, when producing the height of the measurement target 10 in duality, the height of the measurement target 10 may be obtained by the height measurement method of the stereo method having a wide range of the measurable height at the height higher than or equal to the reference height, and the height of the measurement target 10 may be obtained by the height measurement method of the optical triangulation method at the height lower than the reference height.

The control part 130 may be a device capable of performing image processing, shape information processing, calculation, and the like, and may include, for example, a computer. The control part 130 may control the operation of the above components such as the main pattern illumination parts 110a and the main image-capturing parts 120a.

In one embodiment, the control part 130 may control the main pattern illumination part 110a, so that the main image-capturing parts 120a capture an image at the same time while projecting the grating pattern light PL onto the measurement target 10. Alternatively, the control part 130 may control that only a main image-capturing part 120a not adjacent to one main pattern illumination part 110a captures the grating pattern light PL projected onto the measurement target 10.

Meanwhile, each main image-capturing part 120a captures a grating pattern image with being inclined at a predetermined angle in a vertical direction to the measurement target 10, and thus some distortion may be generated as compared with the case of capturing a grating pattern image in a vertical direction to the measurement target 10. Accordingly, the control part 130 may acquire a two-dimensional image or a three-dimensional image captured at the upper portion on the basis of a normal perpendicular to the plane of the measurement target 10 in advance, and then correction of capturing distortion may be performed. The pre-acquired image may be obtained for the measurement target 10 or for a predetermined specimen.

Figure 4:
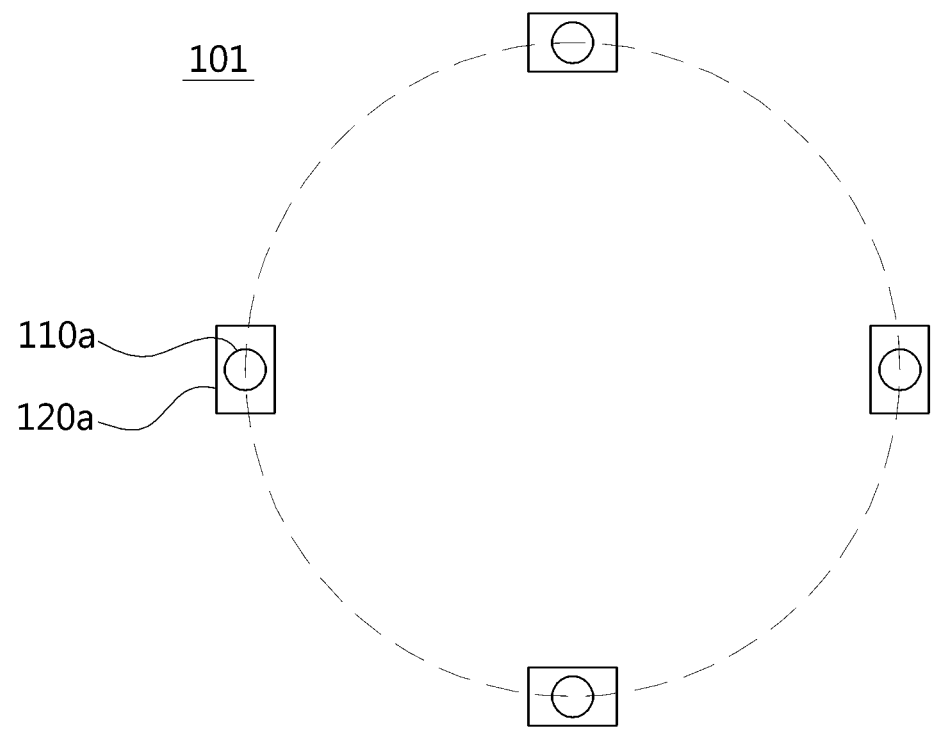
FIG. 4 is a plan view of a three-dimensional shape measurement apparatus according to another exemplary embodiment of the present invention.

FIG. 4 is a plan view of a three-dimensional shape measurement apparatus according to another exemplary embodiment of the present invention.

Referring to FIG. 4, a three-dimensional shape measurement apparatus 101 according to another exemplary embodiment of the present invention may include a plurality of main pattern illumination parts 110a, a plurality of main image-capturing parts 120a, a control part 130 (refer to FIG. 1), a plurality of beam-splitting parts (not shown), etc.

The three-dimensional shape measurement apparatus 101 is substantially the same as the three-dimensional shape measurement apparatus 100 shown in FIGS. 1 and 2 except for the placement configuration of the main pattern illumination parts 110a and the main image-capturing parts 120a, and including the beam-splitting parts. Thus, detailed description thereof will be omitted.

As shown in FIG. 4, the main pattern illumination parts 110a and the main image-capturing parts 120a may be spaced apart from each other around the measurement target 10 in the circumferential direction or arranged at respective vertexes of a polygon around the measurement target 10. The main pattern illumination parts 110a and the main image-capturing parts 120a may be disposed in correspondence with each other. Accordingly, as shown in FIG. 4, the main pattern illumination part 110a and the main image-capturing part 120a that correspond to each other form a set.

The three-dimensional shape measurement apparatus 101 may include a beam-splitting part (not shown), for example, a beam splitter.

The beam-splitting part is disposed corresponding to the main pattern illumination part 110a and the main image-capturing part 120a forming a set. The beam-splitting part transmits the grating pattern light PL generated from the main pattern illumination part 110a toward the measurement target 10, and separates reflection light RL that are emitted from the main pattern illumination parts 110a and reflected by the measurement target 10, to thereby provide the reflection light RL to the main image-capturing part 120a.

In the three-dimensional shape measurement apparatus 101, since the main pattern illumination part 110a, the main image-capturing part 120a and the beam-splitting part are formed to correspond to each other, more compact arrangement of the apparatus and more effective three-dimensional shape measurement of the measurement target 10 may be available.

In this case, the reflection light RL of the grating pattern light PL emitted by one main pattern illumination part 110a may be image-captured by all of the main image-capturing parts 120a, or by main image-capturing parts 120a except for only a main image-capturing part forming the same set with the one main pattern illumination part 110a. In case of capturing by all of the main image-capturing parts 120a, the grating pattern image captured in the main image-capturing part forming the same set with the one main pattern illumination part 110a may be excluded from producing the height data. The operation control and calculation control of the main image-capturing part 120a may be performed by the control part 130.

Figure 5:
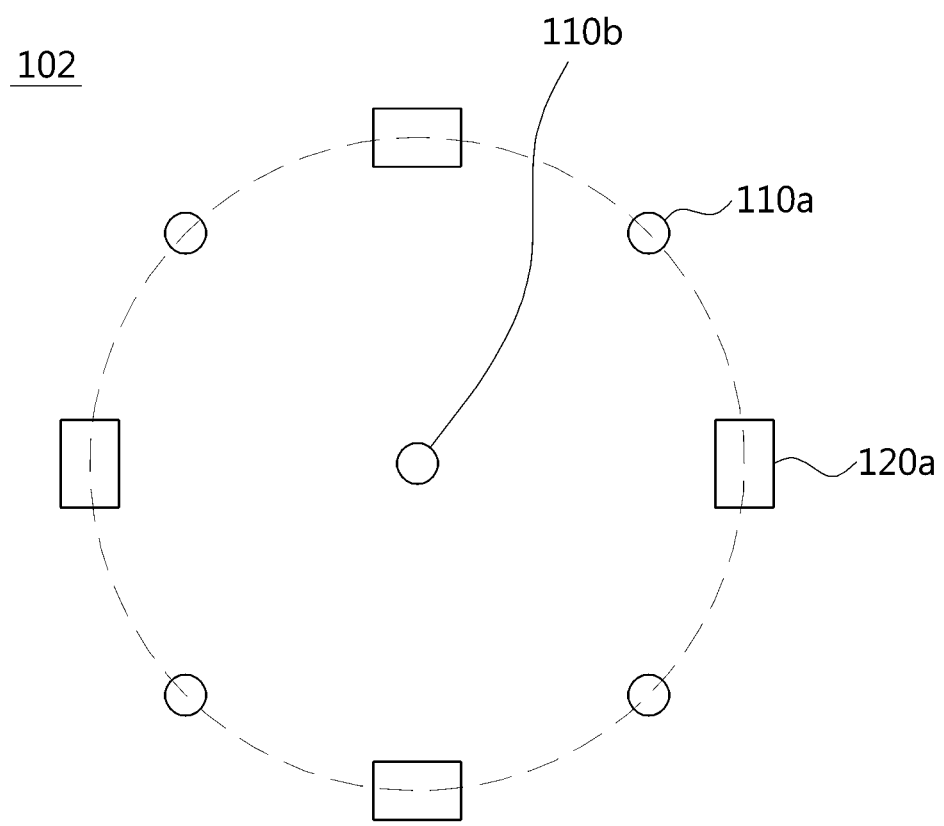
FIG. 5 is a plan view of a three-dimensional shape measurement apparatus according to still another exemplary embodiment of the present invention.

FIG. 5 is a plan view of a three-dimensional shape measurement apparatus according to still another exemplary embodiment of the present invention.

Referring to FIG. 5, a three-dimensional shape measurement apparatus 102 according to still another exemplary of the present invention may include a plurality of main pattern illumination parts 110a, a plurality of main image-capturing parts 120a, a control part 130 (refer to FIG. 1), a top pattern illumination part 110b, etc. The three-dimensional shape measurement apparatus 102 is substantially the same as the three-dimensional shape measurement apparatus 100 shown in FIG. 1 and FIG. 2 except for including the top pattern illumination part 110b. Thus, detailed description thereof will be omitted.

The top pattern illumination part 110b is disposed over the measurement target 10 (refer to FIG. 1), and may vertically provide the grating pattern light PL (refer to FIG. 1) toward the measurement target 10. The grating pattern light PL according to the top pattern illumination part 110b may be simultaneously captured by the main image-capturing parts 120a after being reflected by the measurement target 10.

Meanwhile, the top pattern illumination part 110b may optionally employ optical path changing elements such as a mirror, so that substantial placement positions may be configured as the above, even though actual placement positions are somewhat different from the above.

Thus, since the three-dimensional shape measurement apparatus 102 has the top pattern illumination part 110b, the grating pattern light PL is provided perpendicular to the measurement target 10. Thus, a more accurate three-dimensional shape measurement for the measurement target 10 may be available.

Figure 6:
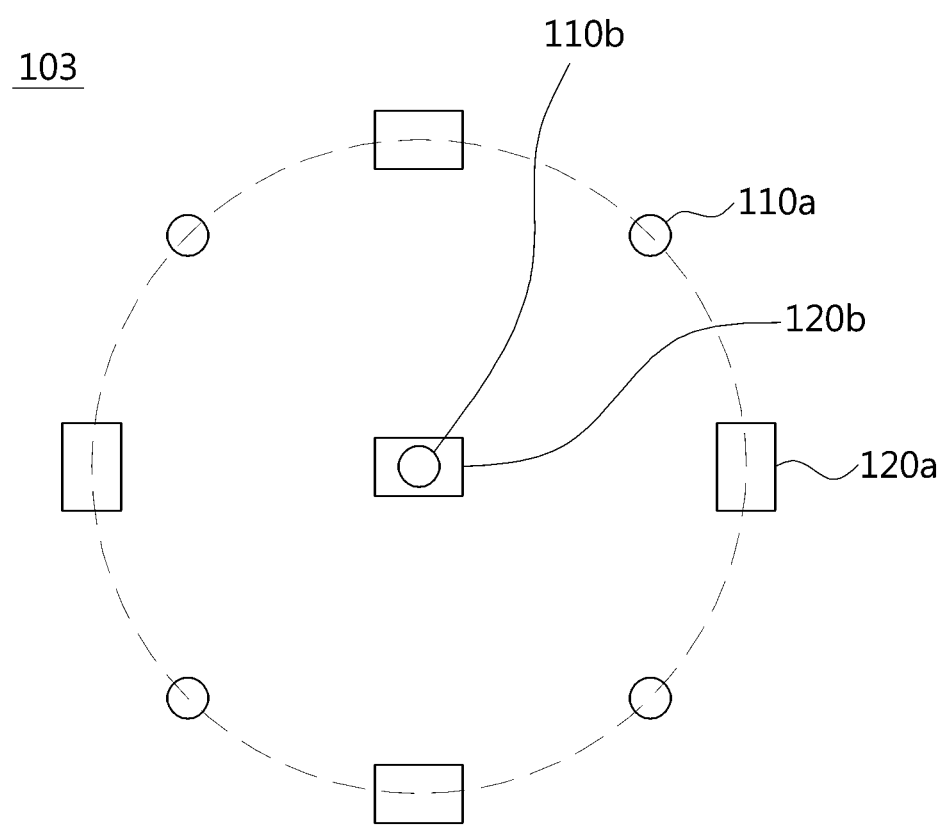
FIG. 6 is a plan view of a three-dimensional shape measurement apparatus according to still another exemplary embodiment of the present invention.

FIG. 6 is a plan view of a three-dimensional shape measurement apparatus according to still another exemplary embodiment of the present invention.

Referring to FIG. 6, a three-dimensional shape measurement apparatus 103 according to still another exemplary of the present invention may include a plurality of main pattern illumination parts 110a, a plurality of main image-capturing parts 120a, a control part 130 (refer to FIG. 1), a top pattern illumination part 110b, a top image-capturing part 120b, etc. The three-dimensional shape measurement apparatus 103 is substantially the same as the three-dimensional shape measurement apparatus 102 shown in FIG. 5 except for including the top image-capturing part 120b. Thus, detailed description thereof will be omitted.

The top pattern illumination part 110b is disposed over the measurement target 10 (refer to FIG. 1), and may capture the grating pattern image that is formed by a process, in which the grating pattern light PL (refer to FIG. 1) is emitted from at least one of the main pattern illumination parts 110a and the top pattern illumination part 110b, and vertically reflected by the measurement target 10, to thereby form the grating pattern image.

In addition, when the illumination part 140 (refer to FIG. 1) is provided, the top image-capturing part 120b may capture a two-dimensional plane image that is formed by a process, in which light emitted from the illumination part 140 and vertically reflected by the measurement target 10, to thereby form the two-dimensional plane image.

That is, the top image-capturing part 120b may image-capture the grating pattern light PL emitted from the top pattern illumination part 110b and then average the captured grating pattern images to generate a two-dimensional plane image in which a grating pattern is removed, and capture a two-dimensional plane image that is formed by a process in which light emitted from the illumination part 140 and vertically reflected by the measurement target 10, to thereby form the two-dimensional plane image. Thus, two-dimensional inspection may be performed based on at least one two-dimensional plane image generated or captured, and the imaging distortion of the measurement target 10 captured by the image-capturing parts 120a may be easily corrected.

The three-dimensional shape measurement apparatus 103 may include a beam-splitting part (not shown), for example, a beam splitter. The beam-splitting part transmits the grating pattern light PL generated from the top pattern illumination part 110b toward the measurement target 10, and reflects at least one of the reflection lights RL that are emitted from the plurality of main pattern illumination parts 110a and the top pattern illumination part 110b and reflected by the measurement target 10, to the top image-capturing part 120b.

Meanwhile, the top image-capturing part 120b may optionally employ optical path changing elements such as a mirror, so that substantial placement positions may be configured as the above, even though actual placement positions are somewhat different from the above.

In FIG. 6, although it is described that the top image-capturing part 120b and the top pattern illumination part 110b are provided together, only the top image-capturing part 120b may be provided without the top pattern illumination part 110b.

Thus, since the three-dimensional shape measurement apparatus 103 has the top image-capturing part 120b, the grating pattern light PL that is vertically reflected is obtained. Thus, a more accurate three-dimensional shape measurement for the measurement target 10 may be available.

Meanwhile, the grating pattern illuminated on the measurement target 10 may be used as the texture information, so that the height data of the measurement target 10 may be also obtained by a stereo method between the top image-capturing part 120b and each main image-capturing part 120a, by which the three-dimensional shape may be measured. Thus, for each field of view (FOV) of the image-capturing part, measurement location or height of the measurement target, main/top illumination parts, main/top image-capturing parts may be selectively image-captured, or an image having high reliability may be selected from captured images, to thereby produce a more accurate three-dimensional shape.

Figure 7:
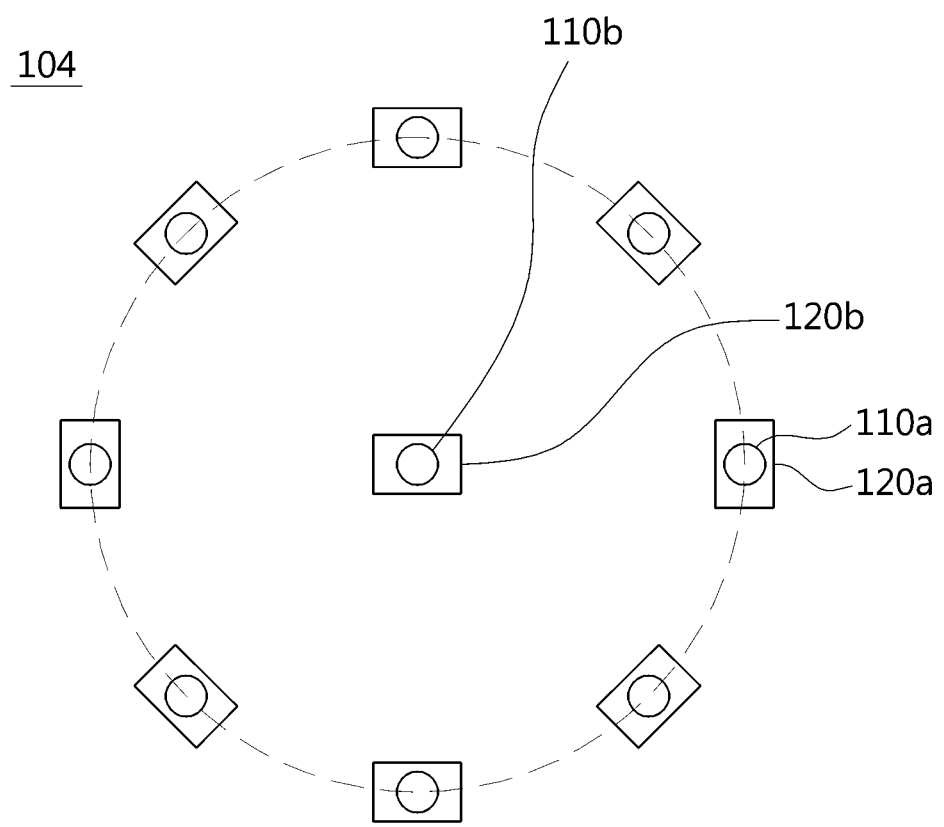
FIG. 7 is a plan view of a three-dimensional shape measurement apparatus according to still another exemplary embodiment of the present invention.

FIG. 7 is a plan view of a three-dimensional shape measurement apparatus according to still another exemplary embodiment of the present invention.

Referring to FIG. 7, a three-dimensional shape measurement apparatus 104 according to still another exemplary of the present invention may include a plurality of main pattern illumination parts 110a, a plurality of main image-capturing parts 120a, a control part 130 (refer to FIG. 1), a top pattern illumination part 110b, a top image-capturing part 120b, a plurality of beam-splitting parts (not shown), etc. The three-dimensional shape measurement apparatus 104 is substantially the same as the three-dimensional shape measurement apparatus 103 shown in FIG. 6 except that the main pattern illumination parts 110a, the main image-capturing parts 120a and the beam-splitting parts 150 are disposed corresponding to each other as shown in FIG. 4. Thus, detailed description thereof will be omitted.

Particularly, the three-dimensional shape measurement apparatus 104 employs the arrangement of the top pattern illumination part 110b and the top image-capturing part 120b shown in FIG. 6, and employs the arrangement of the main pattern illumination parts 110a and the main image-capturing parts 120a shown in FIG. 4.

Thus, it may be possible to include as many pattern illumination parts and image-capturing parts as possible, so that a more precise three-dimensional shape measurement for the measurement target 10 (refer to FIG. 1) may be available.

Meanwhile, in various embodiments of the present invention described above, main/top illumination parts and main/top image-capturing parts arranged for height data acquisition of the measurement target 10 may be possible in various choices and combinations thereof for applying an optical triangulation method or a stereo method. For example, it may be possible to combine the main illumination parts or combine the main illumination part and the top illumination part for applying an optical triangulation method, and it may be also possible to combine main/top image-capturing parts that capture pattern illumination of the illumination parts, apart from the combination of the illumination parts, for applying an optical triangulation method.

In addition, it may be possible to combine main image-capturing parts or combine the main image-capturing part and the top image-capturing part for applying a stereo method. These selections and combinations may be based on various factors such as field of views (FOV) of the image-capturing part, measurement location, height of the measurement target, reliability of the captured image, etc.

According to the present invention described above, in measuring a three-dimensional shape of a measurement target, an optical triangulation method and a stereo measurement method are both or selectively used, in which grating pattern illuminated on the measurement target may be used as texture information of the measurement target in case that it is difficult to utilize the texture information, to thereby measure the three-dimensional shape more easily and accurately.

In addition, in duality based on a predetermined reference height, the optical triangulation method may be used for less than the reference height to produce height data, and the stereo measurement method may be used for greater than or equal to the reference height to produce height data, to thereby maintain measurement accuracy at low height while extending a range of measurable heights.

In addition, by generating grating pattern light from multiple pattern illumination parts and capturing grating pattern images in multiple image-capturing parts, more accurate and precise three-dimensional shape measurement may be available at various directions and angles according to an optical triangulation method and a stereo measurement method.

It will be apparent to those skilled in the art that various modifications and variations may be made in the present invention without departing from the spirit or scope of the invention. Thus, it is intended that the present invention cover the modifications and variations of this invention provided they come within the scope of the appended claims and their equivalents.

The invention claimed is:

1. A three-dimensional shape measurement apparatus comprising:
   a plurality of main pattern illuminators obliquely illuminating grating pattern light in different directions toward a measurement target;
   a plurality of main image-capturing parts obtaining a grating pattern image of the measurement target by receiving reflection light of the grating pattern light that is illuminated from the main pattern illuminators to the measurement target and obliquely reflected by the measurement target; and
   a controller producing height data of the measurement target by selectively applying a first method of producing the height data of the measurement target by using grating pattern images of the measurement target, a second method of producing the height data of the measurement target by using image positions of plane images for the measurement target and texture information of the measurement target, and a third method of producing the height data of the measurement target by utilizing the grating pattern illuminated on the measurement target as the texture information of the measurement target,
   wherein each of the plurality of main-image capturing parts includes a camera and a lens.

2. The three-dimensional shape measurement apparatus of claim 1, further comprising an illuminator illuminating light toward the measurement target,
   wherein the plurality of main image-capturing parts obtain a plane image of the measurement target by receiving reflection light of the light that is illuminated from the illuminator to the measurement target and reflected by the measurement target.

3. The three-dimensional shape measurement apparatus of claim 1, wherein the plane images of the measurement target are image-captured without the grating pattern light or obtained by averaging the grating pattern images.

4. The three-dimensional shape measurement apparatus of claim 1, wherein the controller produces the height data of the measurement target by using the grating pattern images of the measurement target with respect to less than a reference height, and produces the height data of the measurement target by using the image positions of the plane images and for the measurement target and the texture information of the measurement target with respect to the reference height or higher.

5. The three-dimensional shape measurement apparatus of claim 4, wherein the reference height is less than or equal to a measurable height according to the grating pattern light of the main pattern illuminators.

6. The three-dimensional shape measurement apparatus of claim 4, wherein at least two of the main pattern illuminators include gratings having different grating pitches to generate grating pattern lights having different equivalent wavelengths, and
   wherein the reference height is less than or equal to an integrated measurable height according to the different equivalent wavelengths.

7. The three-dimensional shape measurement apparatus of claim 1, further comprising a top pattern illuminator disposed over the measurement target to perpendicularly illuminate grating pattern light toward the measurement target.

8. The three-dimensional shape measurement apparatus of claim 1, further comprising a top image-capturing part disposed over the measurement target to obtain the grating pattern image of the measurement target by receiving reflection light of the grating pattern light that is perpendicularly reflected by the measurement target,
   wherein the top image-capturing part includes a camera and a lens.

9. The three-dimensional shape measurement apparatus of claim 8, wherein the controller produces the height data of the measurement target by using the grating pattern image obtained between the top image-capturing part and each main image-capturing part.

10. The three-dimensional shape measurement apparatus of claim 1, wherein the main pattern illuminators are spaced apart from each other along circumferential direction around the measurement target, and the main image-capturing parts are spaced apart from each other along circumferential direction about the measurement target.

11. The three-dimensional shape measurement apparatus of claim 10, wherein the main pattern illuminators and the main image-capturing parts form one set and are arranged in correspondence with each other.

\* \* \* \* \*